United States Patent [19]

Xu et al.

[11] Patent Number: 5,366,866
[45] Date of Patent: Nov. 22, 1994

[54] METHOD OF DIAGNOSING OVARIAN AND ENDOMETRIAL CANCER WITH MONOCLONAL ANTIBODIES OXA AND OXB

[75] Inventors: Fengi J. Xu; Yinhua Yu, both of Durham; Robert C. Bast, Jr., Chapel Hill, all of N.C.

[73] Assignee: Duke University, Durham, N.C.

[21] Appl. No.: 879,860

[22] Filed: May 6, 1992

Related U.S. Application Data

[63] Continuation-in-part of Ser. No. 735,513, Jul. 26, 1991, abandoned, which is a continuation-in-part of Ser. No. 735,601, Jul. 25, 1991, abandoned.

[51] Int. Cl.$^5$ ............... G01N 33/574; G01N 33/53; G01N 33/567
[52] U.S. Cl. ............... 435/7.23; 435/7.2; 435/7.9; 435/7.92; 436/64; 436/813; 436/518; 436/512; 530/387.7; 530/388.8; 530/388.85; 530/389.7
[58] Field of Search ............ 530/387.7, 388.8, 388.85, 530/389.7; 435/7.2, 7.23, 7.9, 7.92, 973, 975; 436/64, 813, 518, 512

[56] References Cited

U.S. PATENT DOCUMENTS

| | | | |
|---|---|---|---|
| 4,753,894 | 1/1988 | Frankel et al. | 436/548 |
| 4,759,569 | 6/1988 | Teraski et al. | 435/240.27 |
| 4,806,494 | 2/1989 | Pastan et al. | 424/85.91 |
| 4,956,453 | 9/1990 | Bjorn et al. | 530/389 |
| 4,958,009 | 9/1990 | Bjorn et al. | 530/389 |

OTHER PUBLICATIONS

R. Bast, Jr. et al, *A Radioimmunoassay Using a Monoclonal Antibody to Monitor the Course of Eipthelia Ovarian Cancer* The New England Journal of Medicine 309, 883–887 (1983).

R. Bast, Jr. and R. Knapp, *2 Humoral Markers for Epithelial Ovarian Carcinoma in Ovarian Malignancies–Diagnostic and Therapeutic Advances* (M. Piver, Ed. 1987). pp. 11–25.

J. Berek et al., *CA 125 Serum Levels Correlated with Second–Look Operations Among Ovarian Cancer Patients* Obstetrics and Gynecology 67, 685–689 (1986).

R. Young et al., *Cancer of the Ovary in Cancer: Principles and Practices of Oncology* (3d Ed. 1989) (Lippercott) (V. DeVita, S. Hellman S. Rosenberg eds.), pp. 1162–1196.

F.-J. Xu et al., *Development of Two New Monoclonal Antibodies Reactive to a Surface Antigen Present on Human Ovarian Epithelial Cancer Cells* Cancer Research 51, 4012–4019 (1991).

T. Berek and N. Hacker; *Uterine Cancer Practical Gynecologic Oncology* 8, 285–326 (1989).

Klug et al., *Monoclonal Antibody Immuno Radiometric Assay For an Antigenic Determinant CA–125 Associated With Human Epithelial Ovarian Carcinomas* Cancer Res 44, (3) (1984).

A Singhal et al., *Profiles of Lewis$^x$–Containing Glycoproteins and Glycolipids in Sera of Patients with Adenocarcinoma*, Cancer Res. 55, 1375 (1990).

Feller, W. F. et al., *Immunol. Ser.* 53, 631–672 (1990). (abstract only).

Primary Examiner—Toni R. Scheiner
Attorney, Agent, or Firm—Bell, Seltzer, Park & Gibson

[57] ABSTRACT

A method for detecting the presence of cancer employs monoclonal antibody OXA or OXB, antibodies which bind to the antigen bound by monoclonal antibody OXA or OXB, or fragments of the foregoing which bind to the antigen bound by monoclonal antibody OXA or OXB. The method comprises contacting a sample of a biological fluid from a subject with the antibody under conditions permitting the antibody to form a reaction product, and then detecting the presence or absence of the reaction product. The method is particularly useful for monitoring the progression of treatment in a patient previously diagnosed as having ovarian cancer. The method is also useful for detecting and monitoring endometrial cancer.

21 Claims, 2 Drawing Sheets

METHOD OF DIAGNOSING OVARIAN AND ENDOMETRIAL CANCER WITH MONOCLONAL ANTIBODIES OXA AND OXB

This application is a continuation-in-part of Co-pending application Ser. No. 07/735,513, filed Jul. 26, 1991, now abandoned, which is a continuation-in-part of co-pending application Ser. No. 07/735,601, filed Jul. 25, 1991, now abandoned.

FIELD OF THE INVENTION

The present invention relates to the diagnosis of ovarian cancer with monoclonal antibodies in general, and particularly relates to a method of monitoring the response to treatment in an ovarian cancer patient. The present invention also relates to the diagnosis and monitoring of endometrial cancer.

BACKGROUND OF THE INVENTION

Ovarian cancer is the fourth most frequent cause of cancer death among women in the United States. Of all females born in the United States, one of every 70 will develop ovarian cancer and one of every 100 will die from ovarian cancer. See, e.g., R. Young et al., in 1 *Cancer: Principles & Practices of Oncology*, at 1162 (3d ed. 1989)(V. DeVita, S. Hellman, and S. Rosenberg eds.). Similar statistics are reported for many European countries. Ovarian cancer is much more amenable to treatment if detected in its early stages, but is notoriously difficult to detect in its early stages.

The antigenic determinant designated CA125 is the current serum marker of choice for monitoring epithelial ovarian cancer at second look surgical surveillance procedures. CA125 is elevated in serum from 80-90% of ovarian cancer patients, but not in the remaining 10-20% even in the presence of bulky disease. See, e.g., R. Bast et al., *N. Engl. J. Med.* 309, 883-87 (1983). At second look surgical surveillance procedures, CA125 is elevated in 20% of patients (associated with a 96% positive predictive value for the presence persistent disease), while as many as 50-60% of patients with normal CA125 levels have persistent ovarian cancer. See J. Berek et al., *Obstet. Gynecol.* 67, 685-89 (1986). Hence, there has long been a need for a means of monitoring epithelial ovarian cancer supplemental to CA125. Previous studies with potential new markers have, however, identified only 10-20% of patients with persistent disease who have normal CA 125 levels.

The present invention arose from our ongoing efforts to develop new methods of monitoring ovarian cancer.

SUMMARY OF THE INVENTION

Disclosed is a method for detecting the presence of cancer. The method comprises contacting a sample (e.g., a biological fluid) from a subject with an antibody under conditions permitting the antibody to form a reaction product, and then detecting the presence or absence of the reaction product. The antibody may be (a) monoclonal antibody OXA or monoclonal antibody OXB, (b) antibodies (monoclonal or polyclonal) which bind to the antigens bound by monoclonal antibody OXA or OXB, or (c) fragments of (a) or (b) above which bind to the antigens bound by monoclonal antibody OXA or OXB.

The method is particularly useful for detecting ovarian cancer and endometrial cancer. The method may be used to monitor the progression of treatment in a patient previously diagnosed as having cancer or may be used to screen patients who have not been previously diagnosed as having cancer. With respect to the diagnosis and monitoring of ovarian cancer, because the method is complementary to CA125 tests, the method may be carried out on a patient concurrently with testing that patient for elevated CA125 levels, with the combined results providing a superior indication of the presence of cancer than screening or monitoring with CA125 alone. With respect to the diagnosis and monitoring of endometrial cancer, the method may be carried out without concurrently testing the patient for elevated CA125 levels, as CA125 is not highly predictive of endometrial cancer at surgical stage 1 or 2.

DETAILED DESCRIPTION OF THE INVENTION

A. Antibodies and Cell Lines

Antibodies which may be used to carry out the present invention include (a) monoclonal antibody OXA and OXB, (b) antibodies (monoclonal or polyclonal) which bind to the antigen (or more preferably the epitope) bound by monoclonal antibody OXA or OXB, and (c) fragments of (a) or (b) above which bind to the antigen (or more preferably the epitope) bound by monoclonal antibody OXA or OXB. Such antibodies and antibody fragments may be produced by a variety of techniques, as discussed below. The monoclonal antibodies OXA and OXB were developed by F. Xu and Y. Yu in the laboratories of S. Ramakrishnan, as noted below.

The term "antibodies" as used herein refers to all types of immunoglobulins, including IgG, IgM, IgA, IgD, and IgE. Of these, IgM and IgG are particularly preferred. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26, 403-11 (1989). The antibodies may be recombinant monoclonal antibodies produced according to the methods disclosed in Reading U.S. Pat.

No. 4,474,893, or Cabilly et al., U.S. Pat. No. 4,816,567. The antibodies may also be chemically constructed by specific antibodies made according to the method disclosed in Segel et al., U.S. Pat. No. 4,676,980.

Antibodies other than the OXA or OXB antibodies which bind the antigen bound by the OXA or OXB antibodies may be obtained in accordance with known techniques. For example, cells identified as carrying the antigen bound by the OXA or OXB antibody can be washed with an aqueous solution containing a detergent to remove the antigen therefrom, the various fractions in the solution separated by chromatography (e.g., high performance liquid chromatography), and the fraction containing the antigen identified by its ability to bind the OXA or OXB antibody. In the alternative, the OXA or OXB antibody may be immobilized on a solid support to provide an affinity chromatography column, a serum sample from an appropriate patient (e.g., a patient diagnosed as carrying epithelial ovarian cancer) passed through the column, antigen bound to the OXA or OXB antibody eluted from the column, and the antigen used to produce an antibody.

Thus, disclosed herein is a purified antigen produced by the foregoing processes. Such an antigen is recognized by monoclonal antibody OXA or OXB, and has a molecular weight of at least 800 kilodaltons. Alternatively stated, the antigen is a purified antigen having a molecular weight of at least 800 kilodaltons which is expressed by a cell selected from the group consisting of OVCAR-3 and OVCA420 cells, which is not recognized by antibodies which bind to CA125, and which antigen is soluble upon washing a cell which expresses the antigen with a detergent. The antigen may be provided in an aqueous carrier, or in lyophylized form. The antigen may be used to immunize animals to produce polyclonal antibodies, or may be used as an assay standard.

Antibodies which bind to the epitope (i.e., the specific binding site) bound by the OXA or OXB antibody can be identified in accordance with known techniques, such as their ability to compete with labelled OXA or OXB antibody in a competitive binding assay.

Antibody fragments included within the scope of the present invention include, for example, Fab, F(ab')$_2$, and Fv fragments, and the corresponding fragments obtained from antibodies other than IgG. Such fragments can be produced by known techniques.

Polyclonal antibodies used to carry out the present invention may be produced by immunizing a suitable animal (e.g., rabbit, goat, etc.) with an antigen to which monoclonal antibody OXA or OXB binds, collecting immune serum from the animal, and separating the polyclonal antibodies from the immune serum, in accordance with known procedures.

Monoclonal antibodies used to carry out the present invention may be produced in a hybridoma cell line according to the technique of Kohler and Milstein, Nature 265, 495–97 (1975). For example, a solution containing the appropriate antigen may be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable media and the supernatant screened for monoclonal antibodies having the desired specificity.

Monoclonal Fab fragments may be produced in *Escherichia coli* by recombinant techniques known to those skilled in the art. See, e.g., W. Huse, Science 246, 1275–81 (1989).

The hybridoma cell line OXA (also known as OVX1), which produces Monoclonal Antibody OXA, was deposited with the American Type Culture Collection, 12301 Parklawn Drive, Rockville, Md. 20852 USA, in accordance with the provisions of the Budapest Treaty on Jul. 24, 1991, and has been assigned ATCC Accession Number HB10835. This cell line was developed by F. Xu and Y. Yu in the laboratories of S. Ramakrishnan, as noted below.

The hybridoma cell line OXB (also known as OVX2), which produces Monoclonal Antibody OXB, was deposited with the American Type Culture Collection, 12301 Parklawn Drive, Rockville, Md. 20852 USA, in accordance with the provisions of the Budapest Treaty on Jan. 9, 1992, and has been assigned ATCC Accession Number HB10960. This cell line was also developed by F. Xu and Y. Yu in the laboratories of S. Ramakrishnan, as noted below.

B. Subjects

The method disclosed herein may be employed with subjects suspected of carrying cancer (e.g., breast cancer, endometrial cancer or ovarian cancer), particularly ovarian cancer and endometrial cancer, and may be employed both to monitor subjects who have been previously diagnosed as carrying cancer, and to screen subjects who have not been previously diagnosed as carrying cancer. Subjects are typically human females.

The methods disclosed herein are applicable to testing for ovarian cancer, particularly epithelial ovarian cancer. Epithelial ovarian cancer is a well recognized class of ovarian tumors, and includes serous tumors, mucinous tumors, endometrioid tumors, clear cell (mesonephroid) tumors, Brenner tumors, undifferentiated carcinoma, mixed epithelial tumors, and unclassified epithelial tumors. See, e.g., R. Scully, in *Ovarian Malignancies: Diagnostic and Therapeutic Advances*, at 28 (M. Piver ed. 1987).

In a particular embodiment of the methods described herein, the subject has been previously diagnosed as carrying ovarian cancer, and possibly has already undergone treatment for ovarian cancer, and the method is employed to monitor the progression of either that cancer or the treatment thereof. Such monitoring may be carried out preliminary to second look surgical surveillance procedures and subsequent surgical surveillance procedures. For example, samples may be collected from subjects who have received initial surgical treatment for ovarian cancer and subsequent treatment with antineoplastic agents for that cancer to monitor the progress of the treatment.

The present invention is, as noted above, also useful for detecting and monitoring endometrial cancer in human subjects. The term "endometrial cancer" as used herein refers to endometrial cancer of any histological type, including (but not limited to) adenocarcinomas, adenoacanthomas, adenosquamous carcinomas, papillary serous carcinomas, and clear cell carcinomas. See generally J. Berek and N. Hacker, *Practical Gynecologic Oncology* at 294 (1989). The present invention is useful with all patients or patients at risk for endometrial cancer. Patients at risk for endometrial cancer, for whom screening with the method of the present invention is particularly justified, include postmenopausal women on exogenous estrogen treatment, obese postmenopausal women (particularly if there is a family history of endometrial, breast, or ovarian cancer), women whose menopause occurred after 52 years of age, and premenopausal women with anovulatory cycles, such as those with polycystic ovarian disease. J. Berek and N. Hacker, supra at 286.

Diagnosis of ovarian cancer is typically through the identification of a mass on a pelvic examination, though may also be through other means such as radiological diagnosis, pelvic ultrasound, vaginal and cervical cytology, or the detection of a humoral marker such as CA125. Treatment is typically through cytoreductive surgery, followed by treatment with antineoplastic agents (e.g., a combination of cisplatin or carboplatin with an alkylating agent such as cyclophosphamide).

Diagnosis of endometrial carcinoma is typically through an endocervical curretage and endometrial biopsy, as no specific humoral marker is currently available. The treatment for endometrial carcinoma is generally total abdominal hystyerectomy and bilateral salpingooophrectomy. In addition, many patients will require subsequent radiation therapy.

Samples taken from human subjects for use in the methods disclosed herein are generally biological fluids such as serum, blood plasma, or ascites fluid. Serum is presently preferred. In the alternative, the sample taken from the subject can be a tissue sample (e.g., biopsy tissue; scrapings; ovarian tissue removed during surgery; etc.)

C. Immunoassay Formats

Assays carried out in accordance with the present invention may be homogeneous assays or heterogeneous assays. In a homogeneous assay the immunological reaction usually involves the specific antibody (e.g., OXA, OXB), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, coenzymes, and so forth.

In a heterogeneous assay approach, the reagents are usually the specimen, the antibody of the invention (e.g., OXA, OXB), and means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Those skilled in the art will be familiar with numerous specific immunoassay formats and variations thereof which may be useful for carrying out the method disclosed herein. See generally E. Maggio, *Enzyme-Immunoassay,* (1980)(CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." Applicants specifically intend that the disclosures of all U.S. Patent references cited herein be incorporated herein by reference. Monoclonal antibodies as described herein may be used in a "two-site" or "sandwich" assay, with a single cell line serving as a source for both the labeled monoclonal antibody and the bound monoclonal antibody. Such assays are described in U.S. Pat. No. 4,376,110, the disclosure of which is also incorporated herein by reference.

Antibodies as described herein (i.e., OXA, OXB) may be conjugated to a solid support suitable for a diagnostic assay (e.g., beads, plates, slides or wells formed from materials such as latex or polystyrene) in accordance with known techniques, such as precipitation. An antibody or antibody fragment which binds to CA125 may optionally be conjugated to the same support, as discussed below. Antibodies as described herein may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Diagnostic kits for carrying out the methods disclosed above may be produced in a number of ways. In one embodiment, the diagnostic kit comprises (a) an antibody of the invention (e.g., Mab OXA, Mab OXB) conjugated to a solid support and (b) a second antibody of the invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as described herein, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

D. Testing for CA125

The step of detecting the presence of CA125 antigert in a patient, as further indication of whether or not the patient is carrying a cancer, may be carried out concurrently with the method of the present invention. As noted above, elevated levels of CA125 antigen is the current serum marker for ovarian cancer, particularly epithelial ovarian cancer. CA125 may be detected in any suitable manner, but is typically detected by contacting a sample from the patient with an antibody which binds CA125 and then detecting the presence or absence of a reaction product. The antibody may be monoclonal, polyclonal, chimeric, or a fragment of the foregoing, as discussed in detail above, and the step of detecting the reaction product may be carried out with any suitable immunoassay, homogeneous or heterogenous, as also discussed above. The sample from the patient is typically a biological fluid as described above, and may be the same sample of biological fluid used to conduct the method described above (e.g., to which monoclonal antibody OXA or OXB is contacted). Numerous tests for CA125 are known. See, e.g., R. Bast and R. Knapp, in *Ovarian Malignancies: Diagnostic and Therapeutic Advances*, at 11-25 (M. Piver ed. 1987). Such concurrent tests may be employed for both screening of patients who have not been previously diagnosed as carrying ovarian cancer, as well as for monitoring patients who have been previously diagnosed as carrying ovarian cancer.

The present inventions are described in further detail in the following Examples. These Examples are illustrative, and are not to be taken as limiting of the inventions. In the Examples, $\mu l$ means microliters, $\mu g$ means micrograms, mm means millimeters, M means molar, PBS means phosphate-buffered saline, BSA means bovine serum albumin, mCi means milliCuries, cpm means counts per minute as an indication of radioactivity, and temperatures are given in degrees centigrade unless indicated to the contrary.

EXAMPLE 1

Cell Lines and Antibodies

Six ovarian cancer cell lines: OVCAR-3, OVCA420 (obtained from the Dana-Farber Cancer Institute, Boston, Mass.), OVCA429 (Dana-Farber), OVCA432 (Dana-Farber), OVCA433(Dana-Farber), and DOV-13 (Duke); and four breast cancer cell lines: BT20, CAMA-1, MCF7, and SKBr3, were maintained in accordance with standard procedures. See, e.g., S. Ramakrishnan et al., *J. Clin. Invest.* 83, 921-26 (1989).

The normal human foreskin fibroblast cell line Huff, which was obtained from Dr. Kay Singer (Duke University Medical Center) was maintained in Dulbecco's Minimal Essential Medium (DMEM) supplemented with 2mM L-glutamine, 100 U/ml penicillin, 100 $\mu g$/ml streptomycin and 10% heat-inactivated fetal bovine serum (FBS) (Hyclone). The murine myeloma cell line NS-1 was maintained in DMEM supplemented with 2mML-glutamine, 100 U/ml penicillin, 100 $\mu g$/ml streptomycin, 15% FBS, lmM sodium pyruvate, 1% Non Essential Amino Acid and 2% 8-Azaguanine (Sigma).

Murine MAb 317G5, 260F9, 2G3, 520C9 which react with breast cancer, and 454A12 which reacts with the human transferrin receptor (M. Bjorn et al., *Cancer Res.* 45, 1214-21 (1985)) were obtained from Cetus Corporation (Emoryville, Calif.). Murine MAb OVB-3 against ovarian cancer (M. Willingham et al., *Proc. Natl. Acad. Sci. USA* 84, 2474-78 (1987)) was the gift of Dr. Fitz-Gerald (National Institutes of Health). Purified MAb MOV2 and MOV8 against ovarian cancer (E. Tagliabue et al., *Cancer Res.* 45, 379-85 (1985)) were the kind gift of Dr. Maria Colnaghi (Instituto Nazionale Tumori, Milan, Italy). MAb OC125, which reacts with ovarian cancer antigen CA125 (R. Bast et al., *J. Clin. Invest.* 68, 1331-1337 (1981)) was provided by Dr. Robert C. Bast, Jr. (Duke University Medical Center). MAb 19-9, which reacts with gastrointestinal cancer and cross reacts which ovarian cancer (H. Koprowski et al., *Somat. Cell Genet.* 5, 957-72 (1978)) was a gift from Dr. Koprowski.

Control MAb 31E6 is a murine $IgG_1$ that reacts with Thyl.1 and does not react with human ovarian cancer cells, 3B4F11 is a murine IgM that reacts with Obcam protein of bovine brain and negative to human ovarian cancer cells. 31E6 was the gift from Dr. Nowingki and 3B4F11 was obtained from Dr. Sabita Roy.

$^{125}I$ labeled Monoclonal Antibody OC125 was obtained from Centocor.

EXAMPLE 2

Immunization and Production of Hybridomas

This work was conducted by F. Xu and Y. Yu in the laboratories of S. Ramakrishnan at the Duke University Medical Center (Durham, N.C.) and the University of Minnesota (Minneapolis, Minn.).

Antibody-producing hybridomas were generated according to a modification of the original method of Kohler and Milsrein, *Nature* 256, 495-96 (1975). BALB/c mice were immunized intraperitoneally with a single dose of $5 \times 10^6$ of OVCA420 cells (maintained in MEM), then two weeks later with a single dose of $5 \times 10^6$ of OVCA432 cells (maintained in MEM), and then two weeks later with a single dose of $5 \times 10^6$ of OVCAR-3 cells (maintained in RPMI medium), and then two weeks later with a single dose of $5 \times 10^6$ of OVCA420 cells, then one day later with a single dose of $5 \times 10^6$ of OVCA432 cells, and then one day later with a single dose of $5 \times 10^6$ of OVCAR-3 cells. Animals were sacrificed one day after the last injection. For each injection, cells were prepared for injection by aspirating supernatant from the culture flask, then adding trypsin-EDTA solution to release cells according to known procedures, then adding medium back to the flask to neutralize the trypsin, then washing the cells twice with PBS, and then resuspending the cells in PBS at a concentration of $10^7$ cells/ml. Each mouse was injected with 0.5 ml of the final cell suspension. The mice were sacrificed 3 days after the final immunization, spleens removed, and spleen cells prepared for fusion in accordance with standard procedures. The spleen cells were fused with murine myeloma cell line NS-1 in the presence of polyethylene glycol (Boehringer Mannheim's 50% PEG1500) in accordance with manufacturer's instructions to produce hybridoma cells.

Hybridoma cell culture supernatants were screened for reactivity toward 3 immunized cell lines and a normal fibroblast cell line by an enzyme-linked immunosorbent assay (ELISA). Briefly, $5 \times 10^4$ cells per well were plated in a 96 well flat bottom plate (Corning) for 16 to 24 hours. After plating, cells were fixed with 0.25% glutaraldehyde for 10 minutes, then washed with PBS. The "non-specific" binding sites on the wells were blocked by 2% BSA and 2% horse serum in PBS for 30 minutes at room temperature (RT). Wells were rinsed with PBS, 50-100 $\mu l$ of hybridoma culture supernatant was added, and the wells incubated for 60 minutes at RT. The reaction was developed by Vector ABC-AP reagent and phosphatase substrate (2 mg/ml in 100 mM sodium bicarbonate, pH 9.5, 10 mM magnesium chloride)(obtained from Vector Labs Inc., Burlingame, Calif.). Quantitative measurements are made in an ELISA reader (SLT-LABINSTRUMENTS, AUSTRIA). The reaction of 31E6 to all cell lines was as a negative control.

The positive hybridomas were subcloned 3 to 4 times by limiting dilution and maintained in NS-1 medium.

Using serial immunization with the three ovarian cancer cells lines as described herein, two hybridomas (designated OXA and OXB) were obtained which bound to the three cell lines used for immunization but which were negative to the normal fibroblast cell line.

EXAMPLE 3

Isotype and Purification of MAb

This work was conducted by F. Xu and Y. Yu in the laboratories of S. Ramakrishnan at the University of Minnesota.

The target cells OVCAR-3 were plated, fixed and blocked for ELISA. The cells were then incubated 1 hour at room temperature with the OXA and OXB hybridoma supernatants, the plates then washed with PBS and incubated with alkaline phosphatase-labeled anti-mouse Ig, IgM, IgG1, IgG2a, IgG2b, IgG3, Kappa and lambda (SBA Clonotyping System I). After further washes, 100 µl of the phosphatase substrate was added to each well and measuring OD405 in an ELISA reader. The IgM well was positive.

OXA Hybridoma cells were injected to primed BALB/c mice and the ascites were collected after 2 weeks. Purification of MAb was by HPLC. Ascites was precipitated by 60% ammonium sulfate, dialyzed and loaded onto an HPLC gel filtration column (Spherogel TSK 4000 SW, Beckman). MAb was separated from other protein and confirmed by SDS Polyacrylamide gel electrophoresis (SDS-PAGE).

Figure 1A:
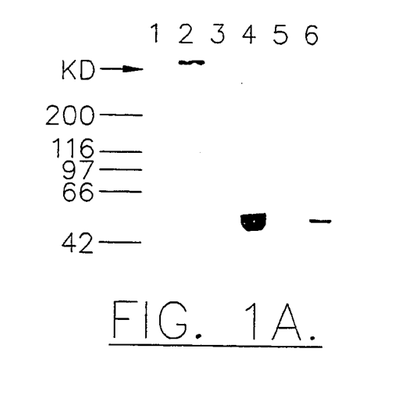
FIG. 1A shows SDS-PAGE analysis of HPLC gel filtration fractions from HPLC gel filtration analysis of OXA ascites as shown in FIG. 1C. Non-reducing 10% gel: fraction 22 (lane 1); fraction 27 (lane 2); fraction 34 (lane 3); fraction 40' (lane 4); fraction 45 (lane 5); fraction 47 (lane 6).
Figure 1B:
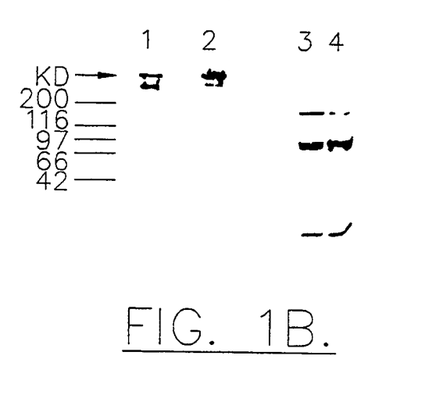
FIG. 1b shows SDS-PAGE analysis of OXA and OXB. Nonreducing 10% gel: OXA (lane 1); OXB (lane 2); reducing: OXA (lane 3); OXB (lane 4).
Figure 1C:
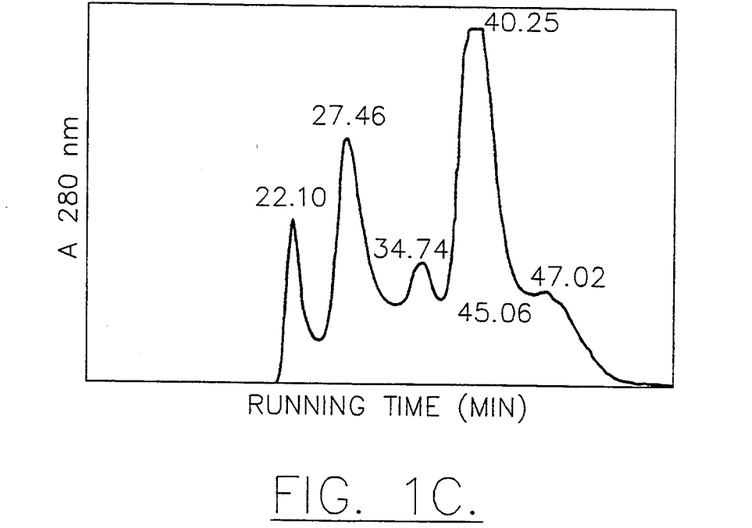
FIG. 1C shows HPLC gel filtration analysis of OXA ascites. OXA ascites was loaded to a gel filtration column (TSK 4000SW) and analyzed in a HPLC system (Beckman). Fractions were collected at intervals of one minute.

Hybridomas OXA and OXB were found to be secreting large amounts of IgM(k). IgM was easily purified by one step of HPLC gel filtration (see FIG. 1).

EXAMPLE 4

Immunohistochemical Staining

This work was conducted by F. Xu and Y. Yu in the laboratories of S. Ramakrishnan at the University of Minnesota.

Human normal or tumor tissues were obtained from the University of Minnesota. Tissues were quickly frozen in liquid nitrogen after removing from human bodies and maintained at $-70°$ C. Frozen tissues were cut in 5-8 um sections in a cryostat at $-15°$ C. The sections were fixed for 10 minutes by acetone, the nonspecific binding sites on the sections blocked by 2% BSA and 2% horse serum, and the sections incubated with MAb (5 µg/ml) overnight at 4° C. The binding ability was detected by developing stain with Vector ABC reagent and DAB substrate (Amersham 0.5 mg/ml).

The slides were counterstained with Harris Hematoxylin (Fisher) and visualized, and then photographed under a light microscope (AH-2, Olympus). Tissue sections were scored and grouped into one of the following categories depending on the intensity of color as: negative, 1+, 2+, and 3+.

Binding of OXA and OXB to human ovarian tissues was evaluated using 6 normal ovary tissues and 20 ovarian cancer tissues. OXA and OXB were positive to 17 and 14 of 20 ovarian cancer tissues, respectively, and negative to 5 and 6 of 6 normal ovary tissues, respectively. 3B4F11, a murine IgM against bovine brain Obcam protein, was a negative control, and was clearly negative to all 20 ovarian cancer tissues and 6 normal ovary tissues. MOV2, an IgM known to bind to ovarian cancer tissue, was a positive control, and it was positive to 10 of these 20 ovarian cancer tissues and negative to 5 of 6 normal ovary tissues. Both MOV2 and OXA were positive to the glands of one normal ovary.

Comparing the binding of OXA and OXB to different ovarian cancer tissues, OXA and OXB revealed different reactions. Binding of OXA was stronger than OXB to most tissues, but with one ovarian adenocarcinoma tissue, OXB bound strongly while OXA was negative.

EXAMPLE 5

Binding Reactivity of Different Cells

This work was conducted by F. Xu and Y. Yu in the laboratories of S. Ramakrishnan at the University of Minnesota.

MAb OXA was labeled with $Na^{125}I$ using the Iodogen method in accordance with known procedures (discussed in greater detail below).

A live cell radioimmunoassay was used to measure binding of MAb to target cells in accordance with known procedures. See Y. Yu et al., *Cancer Res.* 50, 3231-38 (1990). Cells were grown as monolayers, trypsinized and seeded at a density of $1 \times 10^4$ cells/well into 96 well flatbottomed Removawell ® plates (Costar). After overnight incubation at 37° C., the monolayers were washed and different amounts of labeled MAb were added in a volume of 40 µl and incubated on ice for 4 hours. For cross reaction assays, the "cold" MAb was added and incubated on ice for 1 hour before the "hot" labeled MAb was added. Cells were then washed 4 times with ice-cold medium containing 5% FBS. Individual wells were then detached and radioactivity measured therein.

To calculate the binding sites of target cells by radiolabeled MAb, McPherson's "EBDA" program was used. See G. McPherson, *J. Pharmacol. Methods* 14, 213-228 (1985).

Live cell radioimmunoassay as described above revealed the highest binding ratio (B/BO, or "bound-/background") when the labeled MAb was 1 µg/ml. Both OXA and OXB were positive to 5/6 ovarian cell lines and ¾ breast cancer lines, but negative to normal fibroblast cell line Huff.

For calcalating the binding sites of the 2 MABs to target cells-OVCAR3 and OVCA420, a different concentration of labelled MAb is used to saturate or nearly saturate the binding sites of the cells, then binding calcalated by the "EBDA" program. According the calculated results, the binding sites of OXA to OVCAR3 cells is $4.41 \pm 0.39 \times 10^5$ per cell, the binding sites of OXB to OVCAR3 is $1.86 \pm 0.28 \times 10^5$ per cell, the binding sites of OXA to OVCA420 cells is $20.45 \pm 17.54 \times 10^6$ per cell, and the binding sites of OXB to OVCA420 cells is $6.28 \pm 1.95 \times 10^6$ per cell. It is clear that binding sites of OXA-OVCA420 > OXB-OVCA420 > OXA-OVCAR3 > OXB-OVCAR3.

Cross reaction with other MAB. Using the live cell radioimmunoassay, $^{125}I$ labeled OXA and OXB were competed with 10 other MABs against ovarian cancer (i.e., monoclonal antibodies 317G5, 260F9, 2G3, 520C9, 454A12, OVB3, OC125, MOV2, MOV8, and 19-9). For the OVCAR-3 binding assay only OXA and OXB could block their own binding sites and showed cross reactivity to each other. All of the other 10 MABs showed no cross reaction with MABs OXA and OXB.

EXAMPLE 6

Immunofluorescence Assays

This work was conducted by F. Xu and Y. Yu in the laboratories of S. Ramakrishnan at the University of Minnesota.

Normal bone marrow cells and peripheral blood cells were obtained from healthy donors at the University of Minnesota. Cells were suspended in incubation medium (Hank's buffer, 20% FBS, 20 units/ml heparin), then laid on 15 ml of lymphocyte separation medium (Organon Teknika Corporation), centrifuged at 2500 rpm for 15 minuntes, the interface taken, and the cells resuspended in incubation medium for immunofluorescent assay.

Normal peripheral blood cells and bone marrow cells ($5 \times 10^5$) were washed by PBS and 1% FBS and incubated in microfuge tubes with MAb (100 ul of a 5 $\mu$g/ml solution) for 60 minutes on ice, washed 2 times, then incubated with anti-mouse IgG-FITC conjugate (Sigma 1:16) for 30 minutes on ice and washed again. Cells were resuspended in PBS and analyzed in a Flow Cytometer (FACStar plus, Becton Dickinson). FACS analysis revealed that both MABs (OXA and OXB) were negative to normal peripheral blood cells and normal bone marrow cells. Here MAb 31E6 against Thyl.1 was used as a negative control.

EXAMPLE 7

Cell Surface Antigen Solubilization and Immunoblotting

This work was conducted by F. Xu and Y. Yu in the laboratories of S. Ramakrishnan at the University of Minnesota.

Ovarian cancer cell lines OVCAR-3, OVCA420 and normal fibroblast cell line Huff were grown in 100 mm dishes (Falcon) and harvested by cell harvest (Costar), cells were washed twice with Hanks' buffer and solubilized with 20 mM octyl-$\beta$-D-glucopyranoside (O-GP, Calbiochem) in 50 mM Tris buffer (pH 7.4) for 1 hour at room temperature by shaking with a Thermolyne SPECI-MIX mixer. The extract solution was dialyzed in Tris buffer by 4 changes and resolved on 6.5% SDS-PAGE in nonreducing condition. After electrophoresis, the surface antigens were transferred to Immobilon-P membranes (Millipore) in a transblot apparatus (Bio-Rad) at 30my for 18–20 hrs. The blots were blocked by 10% milk, 1% BSA, 0.1% NaN3 and 0.1% tween-20 in PBS for 4 hrs. at RT and probed with designated $^{125}$I-labeled MAb (0.05$\mu$g/ml in 10% milk, 1% BSA, and PBS solution) for 4 hrs. at room temperature by slowing shaking. After 4 times wash with 0.05% Tween-20 in PBS, the blots were air dried and autoradiographed on Kodak X-Omat AR film for 1–7 days at $-70°$ C. using the DuPont Cronex "lightening" enhancing screens.

The surface antigens of target cells OVCAR-3, OVCA420 and control cells Huff were soliblized by O-GP, a nonionic detergent which was intended for use in solubilizing membrane-bound proteins in their native state which has the additional advantage of being removed easily by dialysis. The antigen was a mucin-like protein of such a high molecular weight that it did not penetrate the gel under the conditions used, and therefore was assumed to have a molecular weight greater than 800 kilodaltons.

The Western blot film (see FIG. 2) showed both OXA and OXB bound to high molecular weight surface antigen of OVCAR-3 and OVCA420, the binding ability of 2 MAb to the antigens to OVCA420 cells was much stronger than to OVCAR-3, OXA had stronger binding than OXB to both cell lines.

Figure 2:
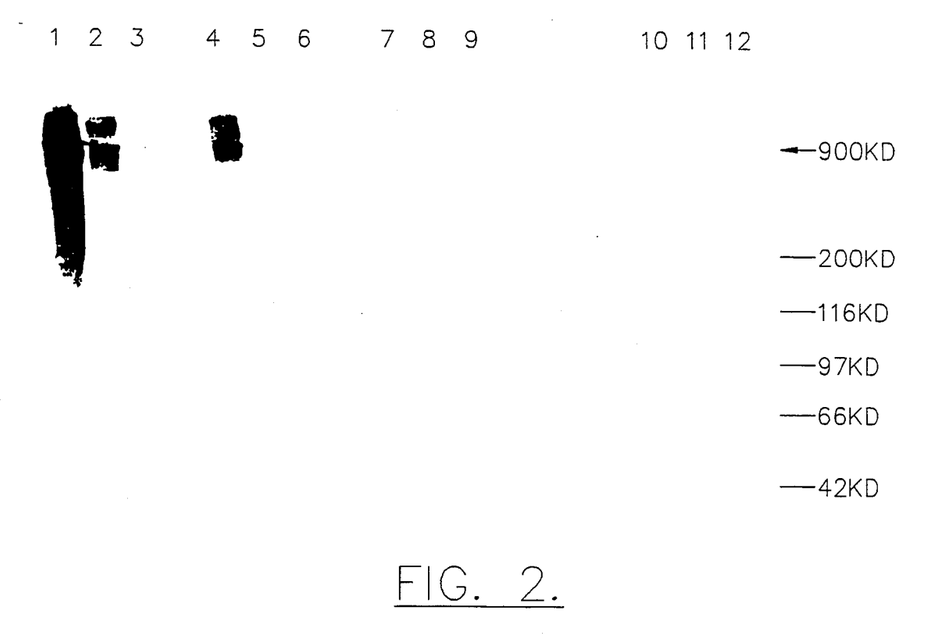
FIG. 2 shows binding of labeled MAB to the antigen solubilized from different cell lines. The antigen extract was subjected to 6.5% SDS-PAGE under non-reducing conditions. Lane 1, 4, 7, and 10: Antigen from OVCA420; lane 2, 5, 8, and 11: Antigen from OVCAR-3; lane 3, 6, 9, and 12: Antigen from Huff. The Western blot was overlaid with $^{125}$I-OXA (lane 1,2,3 0.05 µg/ml); $^{125}$I-OXB (lane 4,5,6, 0.05 µg/ml); $^{125}$I-OC125 (lane 10, 11, 12, 200,000 cpm/ml).

Neither OXA nor OXB bound to Huff cells, the control mouse IgM 3B4F11 did not react with 3 ovarian cancer cell lines. The OC125 MAB, which was known to react with ovarian cancer antigen CA125 (a high molecular glycoprotein complex), did not react with antigens from these cell lines.

EXAMPLE 8

Radioiodination of Monoclonal Antibody OXA

This work was conducted by F. Xu and Y. Yu in the laboratories of R. Bast at Duke University, Durham, N.C.

OXA was labeled with Na$^{125}$I using the Iodogen method. See, e.g., Masuho et al., *Cancer Res.* 44, 2813-19 (1984). In brief, 50 $\mu$l of phosphate buffer (0.5M, pH 7.4) was added to a $15 \times 75$ mm borosilicate tube coated with 10 $\mu$g of Iodogen. Monoclonal antibody (10 $\mu$g in PBS) was added in a volume of 97.5 $\mu$l. Radioiodination was initiated by the addition of 0.25 mCi of Na$^{125}$I (2.5 $\mu$l) and the mixtures were incubated for 20 minutes on ice. The protein-bound iodine was separated by gel filtration on a PD-10 column (Pharmacia, Pleasant Hill, Calif., USA) that had been pre-equilibrated with PBS. A sample of 3 $\mu$l from each 0.5 ml fraction was counted in a Packard gamma counter to measure protein-bound radioactivity. Iodination efficiency was calculated by the following formula:

$$\frac{\text{IODINATION}}{\text{EFFICIENCY}} = \frac{\text{PROTEIN BOUND} \times \text{CPM}}{\text{TOTAL CPM}} \%$$

The efficiency of iodination ranged from 70 to 80%.

EXAMPLE 9

Solid Phase Radioimmunoassays

Radioimmunoassay was conducted in the laboratories of R. Bast at Duke University in essentially the same manner as described in R. Bast et al., *N. Engl. J. Med.* 309, 883-87 (1983). In brief, the assay used polystyrene beads (outer diameter, 6.4mm, Precision Plastic Ball, Chicago, Ill., USA) coated with OXA antibody as a solid-phase immunoadsorbent to bind antigen contained in serum collected from patients. A single coated bead was included in each well of a microtiter plate. Since more than one OXA binding site was associated with each antigen molecule, bound antigen could be detected by simultaneous incubation of the bead and serum sample with $^{125}$I-labeled OXA antibody prepared as described above. Serum (50 $\mu$l) and antigen standards were diluted in buffer (150 $\mu$l PBS with 2% BSA and 2% normal mouse serum) and were incubated simultaneously with polystyrene beads coated with OXA at 4° C. overnight. The beads were washed three times with PBS and then incubated with labeled OXA monoclonal antibody (200,000 cpm/well) at 4° C. overnight. After incubation beads were washed three additional times with PBS to remove excess $^{125}$I-labelled OXA antibody and counted in a Packard gamma counter.

The procedure of the radioimmunoassay may be described in greater detail as follows:

1. Heat Beads (6.4 mm in diameter, Precision Plastic Ball) 80°–100° C. for 1 h, every 15 min shake the beads.
2. Cool down the beads at room temperature.
3. Add OXA (100 μg/ml) in PBS (50 mM $P_i$, pH 7.4, 0.15M NaCl) sit at 37° C. 2 h then 4° C. overnight. Just cover all the beads, no shaking, no rotation.
4. Aspirate the Mab solution for reuse, slowly add 0.25% glutaraldehyde (in PBS). Cover all the beads, sit for 10 min at room temperature.
5. Rinse three times with PBS.
6. Block by 2% BSA+1% normal mouse serum in PBS at 4° C. overnight.
7. Directly put the beads in multiplate. One bead each well.
8. Five standards and two controls were run with sera
   a) standard Ag: (20 μg/ml, 10 μg/ml, 4 μg/ml, 2 μg/ml, 1 μg/ml)
   b) control two sera—one low level and one high level
9. Pipette 50 μl of standard controls and specimen samples into their assigned wells (duplicate). Add blocking solution (2% BSA+1% normal mouse serum in PBS) 150 μl each well, incubate in duplicate overnight at 4° C.
10. Wash three times with PBS.
11. Add 200 μl of $^{125}$I-Mab OXA (1000 cpm/μl) diluted in blocking buffer, incubate at 4° C. overnight.
12. Wash three times with PBS.
13. Gamma count.
14. To determine background, beads coated with OXA antibody are incubated with blocking buffer alone.
15. Monoclonal antibody was labeled with Na $^{125}$I using an Iodogen method. In brief, 50 μl of phosphate buffer (0.5M, pH 7.4) was added to a 15×75 mm borosilicate tube coated with 10 μg of Iodogen. Mab (10 μg in PBS) was added in a volume of 97.5 μl. Radioiodination was initiated by the addition of 0.25 mCi of Na $^{125}$I (2.5 μl) and the mixtures were incubated for 20 min on ice. The protein-bound iodine was separated by gel filtration on a PD-10 column (Pharmacia, Pleasant Hill, Calif.) that had been preequilibrated with PBS. A sample of 3 μl from each fraction was counted in a Packard gamma counter to measure protein-bound radioactivity. Iodination efficiency was calculated by the formula given above.

As shown in Tables 1 and 2 below, OXA antigen level is elevated in 62% of patients with negative CA125 values and positive second look surgical procedures. Each data point shown is the mean of duplicate samples. In Table 1, "CED" means clinically evident disease, "+BX" means palpable tumor with positive biopsy, and "POP" means pre-operative specimen at time of diagnosis. In Table 2, "+2ND" means positive second look surgical surveillance procedure and "+3RD" means positive third look surgical surveillance procedure. An OXA value of 6.26 was employed as the cutoff above which the OXA assay was considered positive, with 6.26 representing the mean OXA value plus two standard deviations found in a sample of 104 healthy controls.

TABLE 1

| Record Number | CA125 Date | Look2 Date | Status | CA125 Value[1] | OXA Value[2] |
|---|---|---|---|---|---|
| 66 | 5/18/81 | — | CED | 7.2 | 0.8 |
| 45 | 1/23/85 | — | +BX | 25.8 | ND |
| 65 | 3/28/85 | — | CED | 14.2 | 16.8 |
| 62 | 11/12/85 | — | CED | 29.4 | 35.6 |
| 44 | 2/26/86 | — | +BX | 19.0 | 8.4 |
| 63 | 3/6/86 | — | CED | 6.5 | 10.4 |
| 64 | 5/15/86 | — | CED | 22.6 | 11.2 |
| 51 | 9/26/86 | — | CED | 7.6 | 4.8 |
| 52 | 11/13/86 | — | CED | 3.7 | 16.8 |
| 54 | 2/11/87 | — | CED | 16.6 | 3.2 |
| 55 | 3/19/87 | — | CED | 33.9 | 4.8 |
| 56 | 4/20/87 | — | CED | 33.9 | 10.4 |
| 57 | 4/20/87 | — | CED | 13.1 | 1.6 |
| 41 | 5/20/87 | — | POP | 11.3 | 28.4 |
| 58 | 5/20/87 | — | CED | 23.7 | 4.8 |
| 59 | 7/13/87 | — | CED | 15.5 | 2.8 |
| 60 | 7/13/87 | — | CED | 21.3 | 3.2 |
| 61 | 7/28/87 | — | CED | 15.1 | ND |
| 48 | — | — | CED | 5.6 | ND |
| 49 | — | — | CED | 0.5 | 2.4 |

[1] A CA125 value greater than 35 is positive.
[2] An OXA value greater than 6.26 is positive. Values greater than 6.26 are underlined.

TABLE 2

| Record Number | CA125 Date | Look2 Date | Status | CA125 Value[1] | OXA Value[2] |
|---|---|---|---|---|---|
| 12 | 4/27/81 | 4/29/82 | +2ND | 6.6 | 0.8 |
| 13 | 9/3/825 | 9/14/82 | +2ND | 4.0 | 0.8 |
| 18 | 5/27/84 | 5/29/84 | +2ND | 9.6 | 31.2 |
| 39 | 1/15/85 | 1/15/85 | +2ND | 7.2 | 18.4 |
| 14 | 1/16/85 | 1/16/85 | +2ND | 7.5 | 5.2 |
| 15 | 4/16/85 | 4/16/85 | +2ND | 8.3 | 10.0 |
| 19 | 7/8/85 | 7/8/85 | +2ND | 11.4 | 29.2 |
| 10 | 7/11/85 | 7/15/85 | +2ND | 20.7 | 11.2 |
| 21 | 9/10/85 | 9/11/85 | +2ND | 8.3 | 19.2 |
| 4 | 9/20/85 | 9/20/85 | +2ND | 5.7 | 1.6 |
| 17 | 3/3/86 | 3/4/86 | +2ND | 13.7 | 16.8 |
| 32 | 3/6/85 | 6/3/86 | +2ND | 8.0 | 24.4 |
| 27 | 4/14/86 | 4/14/86 | +2ND | 25.5 | 34.8 |
| 28 | 5/6/86 | 5/6/86 | +2ND | 8.6 | 9.6 |
| 20 | 6/30/86 | 7/2/86 | +2ND | 15.7 | 6.8 |
| 11 | 8/11/86 | 8/11/86 | +2ND | 20.9 | ND |
| 24 | 9/22/86 | 9/24/86 | +2ND | 21.5 | ND |
| 22 | 10/13/86 | 10/13/86 | +2ND | 10.9 | 10.8 |
| 2 | 10/21/86 | 10/21/86 | +2ND | 5.2 | 17.2 |
| 1 | 10/27/86 | 10/27/86 | +2ND | 5.3 | 0.4 |
| 8 | 12/20/86 | 1/2/87 | +2ND | 3.7 | 25.6 |
| 23 | 6/22/87 | 6/24/87 | +2ND | 6.5 | 9.6 |
| 29 | 7/15/87 | 7/15/87 | +2ND | 14.2 | 11.2 |
| 43 | 8/13/87 | — | +3RD | 9.9 | 2.4 |
| 3 | 11/1/87 | 11/1/87 | +2ND | 8.4 | 7.2 |
| 30 | 1/5/88 | 1/6/88 | +2ND | 15.0 | 7.2 |
| 38 | 4/12/88 | 4/21/88 | +2ND | 11.1 | 2.4 |
| 36 | 4/18/88 | 4/19/88 | +2ND | 5.4 | 0.4 |
| 6 | 12/19/88 | 12/15/88 | +2ND | 12.2 | 6.4 |
| 5 | 6/13/89 | 6/14/89 | +2ND | 1.5 | 0.8 |
| 34 | 6/28/89 | 6/28/89 | +2ND | 4.3 | 0.4 |
| 40 | 12/18/89 | 12/28/89 | +2ND | 15.3 | 7.6 |

[1] A CA125 value greater than 35 is positive.
[2] An OXA value greater than 6.26 is positive. Values greater than 6.26 are underlined.

EXAMPLE 10

OXA Antigen Purification

This work was conducted by F. Xu and Y. Yu in the laboratories of R. Bast at Duke University, Durham, N.C.

OVCA 420 Cells (150×10$^6$) were harvested by scraping and washing twice with Hanks' buffered saline, resuspended in 10 ml O-GP solution (octyl-β-D-glucopyranoside, 20 mM in 50 mM Tris, pH 7.4), rotated at room temperature for 2 hours, and sedimented 5 minutes in a microcentrifuge at 14,000 rpm. The supernatant was dialyzed in 50 mM Tris buffer, pH 7.4, overnight and then chromatographed on an HPLC TSK-G3000 column. The activity of each peak is monitored with the OXA radioimmunoassay and the peak most reactive in the radioimmunoassay was concentrated to 1 mg/ml.

EXAMPLE 11

Radioiodination of Monoclonal Antibody OXB

OXB is labeled with $Na^{125}I$ using the Iodogen method essentially as described in connection with the labeling of OXA in Example 8 above. In brief, 50 µl of phosphate buffer (0.5 SM, pH 7.4) is added to a 15×75 mm borosilicate tube coated with 10 µg of Iodogen. Monoclonal antibody (10 µg in PBS) is added in a volume of 97.5 µl. Radioiodination is initiated by the addition of 0.25 mCi of $Na^{125}I$ (2.5 µl) and the mixtures are incubated for 20 minutes on ice. The protein-bound iodine is separated by gel filtration on a PD-10 column (Pharmacia, Pleasant Hill, Calif., USA) that is preequilibrated with PBS. A sample of 3 µl from each 0.5 ml fraction is counted in a Packard gamma counter to measure protein-bound radioactivity. Iodination efficiency is calculated by the formula given in Example 8 above.

EXAMPLE 12

Solid Phase Radioimmunoassay with OXB

Radioimmunoassay is conducted in essentially the same manner as described in connection with radioimmunoassay with OXA in Example 9 above. In brief, the assay uses polystyrene beads (outer diameter, 6.4 mm, Precision Plastic Ball, Chicago, Ill., USA) coated with OXB antibody as a solid-phase immunoadsorbent to bind antigen contained in serum collected from patients. A single coated bead is included in each well of a microtiter plate. Since more than one OXB binding site is associated with each antigen molecule, bound antigen is detected by simultaneous incubation of the bead and serum sample with $^{125}I$-labeled OXB antibody prepared as described above. Serum (50 µl) and antigen standards are diluted in buffer (150 µl PBS with 2% BSA and 2% normal mouse serum) and incubated simultaneously with polystyrene beads coated with OXB at 4° C. overnight. The beads are washed three times with PBS and then incubated with labeled OXB monoclonal antibody (200,000 cpm/well) at 4° C. overnight. After incubation beads are washed three additional times with PBS to remove excess $^{125}I$-labelled OXB antibody and counted in a Packard gamma counter.

The details of the radioimmunoassay procedure are essentially the same as given in Example 9 above, except that OXB is substituted for OXA.

EXAMPLE 13

OXB Antigen Purification

The three cell lines used in the serial immunizations described in Example 2 above are assayed for the presence of OXB antigen with the labeled OXB antibody described in Example 8 above. The positive cells are harvested by scraping and washing twice with Hanks' buffered saline, resuspended in 10 ml O-GP solution (octyl-β-D-glucopyranoside, 20mM in 50mM Tris, pH 7.4), rotated at room temperature for 2 hours, and sedimented 5 minutes in a microcentrifuge at 14,000 rpm. The supernatant is dialyzed in 50 mM Tris buffer, pH 7.4, overnight and then chromatographed on an HPLC TSK-G3000 column. The activity of each peak is monitored with the OXB radioimmunoassay and the peak most reactive in the radioimmunoassay was concentrated to 1 mg/ml.

EXAMPLE 14

Detection of Endometrial cancer With MAb OXA

This example was carried out in essentially the same manner as Example 9 above, except that sera was collected from patients in various surgical stages of endometrial cancer prior to surgery. Surgical stage represents the severity of disease, Stage I being least severe and Stage IV being the most severe, as determined after a surgery in accordance with the same criteria employed in the FIGO Staging for endometrial carcinoma, see J. Berek and N. Hacker, *Practical Gynecologic Oncology*, 289–291 (1991), as is known in the art. The data, including that for monoclonal antibody CA125, are given in Table 3 below. An OXA value of 7.2 was employed as the cutoff above which the OXA assay was considered positive, with 7.2 representing the mean OXA value plus two standard deviations found in a sample of 184 healthy controls. The data for each antibody is presented first as a proportion of positive reactions over the total number of patients in that sample, and then as a percentage of positive reactions for that sample- OXA values greater than 7.2 and CA125 values greater than 35 are considered positive, respectively. The data show that OXA was more effective than CA125 in detecting endometrial cancer. For example, of 48 patients in surgical stage 1, 34 (or 71%) were positive as determined by OXA, but only 9 (or 19%) were positive as determined by CA125. Moreover, OXA appeared much more effective in detecting endometrial cancer at an early surgical stage, where the probability of successful treatment is greater. Also significant is the fact that a positive result with OXA was seen in only 3 of 21 patients afflicted with endometriosis (but not endometrial cancer) (data not shown). These data indicate that the OXA monoclonal antibody is useful for detecting endometrial cancer.

TABLE 3

| Surgical Stage | OXA (+) | | CA125 (+) | |
| --- | --- | --- | --- | --- |
| 1 | 34/48 | 71% | 9/48 | 19% |
| 2 | 3/3 | 100% | 0/3 | 0 |
| 3 | 5/7 | 71% | 0/7 | 0 |
| 4 | 5/5 | 100% | 5/5 | 100% |
| Total | 47/63 | 75% | 14/63 | 22% |

The foregoing examples are illustrative of the present invention, and are not to be construed as limiting thereof. The invention is defined by the following claims, with equivalents of the claims to be included therein.

That which is claimed is:

1. A method of screening for the presence of cancer in a human subject, the cancer selected from the group consisting of ovarian, breast and endometrial cancer, the method comprising:

contacting a sample comprising a biological fluid taken from said subject with an antibody selected from the group consisting of monoclonal antibody OXA, monoclonal antibody OXB, antibodies which specifically bind the epitope bound by monoclonal antibody OXA or OXB, and fragments thereof which specifically bind the epitope bound by monoclonal antibody OXA or OXB, under conditions permitting said antibody to specifically bind an antigen in the sample to form an antibody-antigen complex; and then determining the amount of antibody-antigen complex in the sample as a measure of the amount of antigen in the sample, wherein an elevated level of the antigen in the sample is associated with the presence of ovarian, breast or endometrial cancer.

2. A method according to claim 1, wherein said cancer is selected from the group comprising ovarian cancer and breast cancer.

3. A method according to claim 1, wherein said cancer is epithelial ovarian cancer.

4. A method according to claim 1, wherein said subject has not been previously diagnosed as carrying cancer.

5. A method according to claim 1, which method is selected from the group consisting of radioimmunoassay, immunofluorescence assay, and enzyme immunoassay.

6. A method according to claim 1, wherein said biological fluid is selected from the group consisting of serum, blood plasma, and ascites fluid.

7. A method according to claim 1, wherein said biological fluid is selected from the group consisting of serum and blood plasma.

8. A method according to claim 1, further comprising the step of concurrently detecting the presence of CA125 antigen in said subject.

9. A method of screening for the presence of epithelial ovarian cancer in a human subject, comprising:

contacting a sample comprising a biological fluid collected from said subject with an antibody, wherein said subject has been previously diagnosed as carrying epithelial ovarian cancer, and wherein said antibody is selected from the group consisting of monoclonal antibody OXA, monoclonal antibody OXB, antibodies which specifically bind the epitope bound by monoclonal antibody OXA or OXB, and fragments thereof which specifically bind the epitope bound by monoclonal antibody OXA or OXB, under conditions permitting said antibody to specifically bind an antigen in the sample to form and antibody-antigen complex; and then determining the amount of antibody-antigen complex in the sample as a measure of the amount of antigen in the sample, wherein an elevated level of the antigen in the sample is associated with the presence of epithelial ovarian cancer.

10. A method according to claim 9, wherein said subject has previously undergone treatment for ovarian cancer.

11. A method according to claim 9, said antibody selected from the group consisting of monoclonal antibody OXA, monoclonal antibody OXB, monoclonal antibodies which bind to the epitope bound by monoclonal antibody OXA or OXB, and fragments thereof which bind to the epitope bound by monoclonal antibody OXA or OXB.

12. A method according to claim 9, which method is selected from the group consisting of radioimmunoassay, immunofluorescence assay, and enzyme immunoassay.

13. A method according to claim 9, wherein said biological fluid is selected from the group consisting of serum, blood plasma, and ascites fluid.

14. A method according to claim 9, wherein said biological fluid is selected from the group consisting of serum and blood plasma.

15. A method according to claim 9, further comprising the step of concurrently detecting the presence of CA125 antigen in said subject.

16. A method of screening for the presence of endometrial cancer in a human subject, comprising:

contacting a sample comprising a biological fluid collected from said subject with an antibody selected from the group consisting of monoclonal antibody OXA, monoclonal antibody OXB, antibodies which specifically bind the epitope bound by monoclonal antibody OXA or OXB, and fragments thereof which specifically bind the epitope bound by monoclonal antibody OXA or OXB, under conditions permitting said antibody to specifically bind an antigen in the sample to form and antibody-antigen complex; and then determining the amount of antibody-antigen complex in the sample as a measure of the amount of antigen in the sample, wherein an elevated level of the antigen in the sample is associated with the presence of endometrial cancer.

17. A method according to claim 16, said antibody selected from the group consisting of monoclonal antibody OXA, antibodies which bind to the epitope bound by monoclonal antibody OXA, and fragments thereof which bind to the epitope bound by monoclonal antibody OXA.

18. A method according to claim 16, wherein said subject has not been previously diagnosed as carrying cancer.

19. A method according to claim 16, wherein said biological fluid is selected from the group consisting of serum, blood plasma, and ascites fluid.

20. A method according to claim 16, wherein said biological fluid is selected from the group consisting of serum and blood plasma.

21. A method according to claim 1, wherein said cancer is breast cancer.

* * * * *